United States Patent
Kim et al.

(10) Patent No.: US 9,065,056 B2
(45) Date of Patent: Jun. 23, 2015

(54) SEMI-FLUOROALKYL GROUP SUBSTITUTED ORGANIC SEMICONDUCTOR POLYMER AND ORGANIC THIN FILM TRANSISTOR INCLUDING THE SAME

(71) Applicant: GWANGJU INSTITUTE OF SCIENCE AND TECHNOLOGY, Gwangju (KR)

(72) Inventors: Dong-Yu Kim, Gwangju (KR); Hyung-Gu Jeong, Gwangju (KR); Bogyu Lim, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 0 days.

(21) Appl. No.: 14/057,436

(22) Filed: Oct. 18, 2013

(65) Prior Publication Data
US 2014/0110689 A1      Apr. 24, 2014

(30) Foreign Application Priority Data

Oct. 18, 2012  (KR) .......................... 10-2012-0115984

(51) Int. Cl.
*H01L 51/00* (2006.01)
*C07D 409/14* (2006.01)
*C08G 61/12* (2006.01)
*H01L 51/05* (2006.01)

(52) U.S. Cl.
CPC .......... *H01L 51/0036* (2013.01); *C07D 409/14* (2013.01); *C08G 61/126* (2013.01); *C08G 2261/146* (2013.01); *C08G 2261/3223* (2013.01); *C08G 2261/364* (2013.01); *C08G 2261/411* (2013.01); *H01L 51/0007* (2013.01); *H01L 51/0545* (2013.01)

(58) Field of Classification Search
USPC ............................................. 549/59
See application file for complete search history.

(56) References Cited

U.S. PATENT DOCUMENTS 7,250,625 B2 *  7/2007  Ong et al. ........................ 257/40

OTHER PUBLICATIONS

Jeong et al., A Novel Thermally Reversible Soluble-Insoluble Conjugated Polymer with Semi-Fluorinated Alkyl Chains: Enhanced Transistor Performance by Fluorophobic Self-Organization and Orthogonal Hydrophobic Patterning, 2013, Adv. Mater., 25, 6416-6422.*

* cited by examiner

*Primary Examiner* — Kristin Vajda
(74) *Attorney, Agent, or Firm* — Lowe Hauptam & Ham, LLP

(57) ABSTRACT

A semi-fluoroalkyl group substituted organic semiconductor polymer and an organic thin film transistor including the same are disclosed. A structure in which hydrogen of only a terminal of an alkyl group is substituted with fluorine exhibits significantly increased hole mobility, and significantly improved properties in terms of thermal stability and chemical stability, as compared to a structure in which all hydrogens coupled to a thiophene ring are substituted with fluorine, or a structure in which hydrogen of the terminal thereof is not substituted with fluorine and only hydrogens of the remaining portion are coupled to the thiophene ring.

4 Claims, 10 Drawing Sheets

SEMI-FLUOROALKYL GROUP SUBSTITUTED ORGANIC SEMICONDUCTOR POLYMER AND ORGANIC THIN FILM TRANSISTOR INCLUDING THE SAME

CROSS-REFERENCE TO RELATED APPLICATION

This application claims priority to Korean Patent Application No. 10-2012-0115984 filed on 18 Oct. 2012, and all the benefits accruing therefrom under 35 U.S.C. §119, the contents of which is incorporated by reference in its entirety.

BACKGROUND

1. Technical Field

The present invention relates to a semi-fluoroalkyl group substituted organic semiconductor polymer and an organic thin film transistor including the same.

2. Description of the Related Art

PQT-12 polymers, which are widely known as an organic semiconductor material, are composed of bithiophene units having a dodecyl side chain at the C-3 position of thiophene and bithiophene units having an unsubstituted alkyl side chain, and it is known that bithiophene units having an unsubstituted alkyl side chain exhibit high crystallinity and excellent hole mobility of 0.12 cm$^2$/Vs to 0.2 cm$^2$/Vs in OFET-based devices, since the polymer side chains thereof provide a space for interdigitation.

However, the aforementioned hole mobility is exhibited when thin films are prepared by spin-coating, and formation of thin films using spin-coating has a great disadvantage in that most polymer materials are wasted. In addition, since high hole mobility of PQT-12 polymer is a level capable of being obtained by improving crystallinity of the polymer through an additional thermal annealing process at 140° C., the PQT-12 polymer disadvantageously exhibits a low hole mobility of 0.02 cm$^2$/Vs to 0.05 cm$^2$/Vs if thermal annealing is not performed.

One compound of the PQT-12 polymer is a polymer shown below, and a repeat number of repeat units is omitted for convenience.

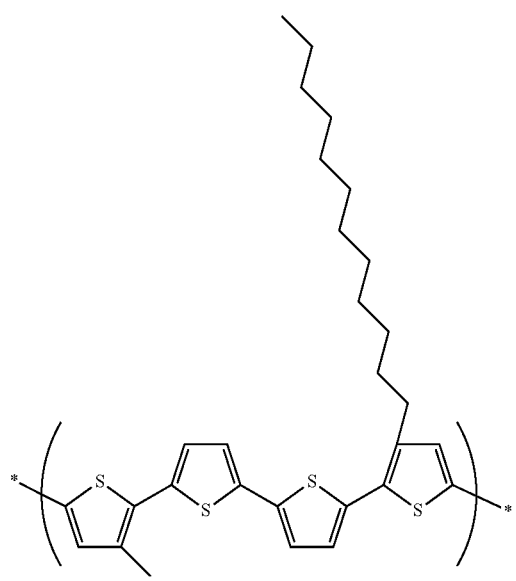

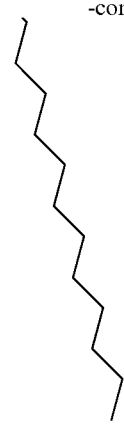

BRIEF SUMMARY

Embodiments of the present invention provide the following effects:

(1) Improvement of hole mobility of conductive organic thin films;

(2) Improvement of thermal stability and chemical stability of conductive organic thin films;

(3) Easy realization of a bi-layer of an n-type polymer and a p-type polymer; (4) Provision of a method of enabling conductive organic thin films to be prepared without thermal annealing;

(5) Provision of a method of enabling large area devices to be prepared by obtaining desired effects using only dip-coating instead of spin-coating;

(6) Thermally reversible soluble-insoluble property; and (7) Easy realization of a patterning process by hydrophobic surface of conductive organic thin films.

It is one aspect of the present invention to provide a π-conjugated compound represented by Formula 1 and a method of preparing the same.

[Formula 1]

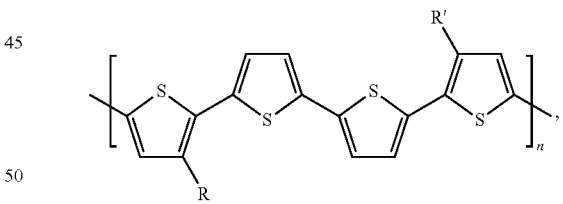

wherein R and R' are the same or different, each independently a $C_8$ to $C_{16}$ linear alkyl group, and composed of a fluorine-unsubstituted alkyl group and a fluorine-substituted alkyl group, wherein the fluorine-unsubstituted alkyl group is an alkyl group coupled to a thiophene ring of Formula 1; the fluorine-substituted alkyl group is an alkyl group in which all hydrogens bonded to carbon are substituted with fluorine, and is coupled to the fluorine-unsubstituted alkyl group to constitute terminals of R and R' linear alkyl groups; a carbon number of the fluorine-substituted alkyl group is 0.5 to 2 times the carbon number of the fluorine-unsubstituted alkyl group; and n is an integer of 2 or more.

It is another aspect of the present invention to provide a conductive organic thin film including the π-conjugated compound according to the present invention.

It is a further aspect of the present invention to provide an organic field effect transistor, which includes a source electrode, a drain electrode, a gate electrode, a gate insulating layer, and an organic semiconductor layer, wherein the organic semiconductor layer includes the aforementioned conductive organic thin film.

According to embodiments of the present invention, the following effects may be achieved:

(1) Improvement of hole mobility of conductive organic thin films;

(2) Improvement of thermal stability and chemical stability of conductive organic thin films;

(3) Easy realization of a bi-layer of an n-type polymer and a p-type polymer;

(4) Enabling conductive organic thin films to be prepared without thermal annealing;

(5) Enabling large area devices to be prepared by obtaining desired effects using only dip-coating instead of spin-coating;

(6) Thermally reversible soluble-insoluble property of a π-conjugated compound; and (7) Easy realization of a patterning process by hydrophobic surface of conductive organic thin films.

BRIEF DESCRIPTION OF THE DRAWINGS

The above and other aspects, features, and advantages of the present invention will become apparent from the detailed description of the following embodiments in conjunction with the accompanying drawings, in which.

DETAILED DESCRIPTION

Figure 1:
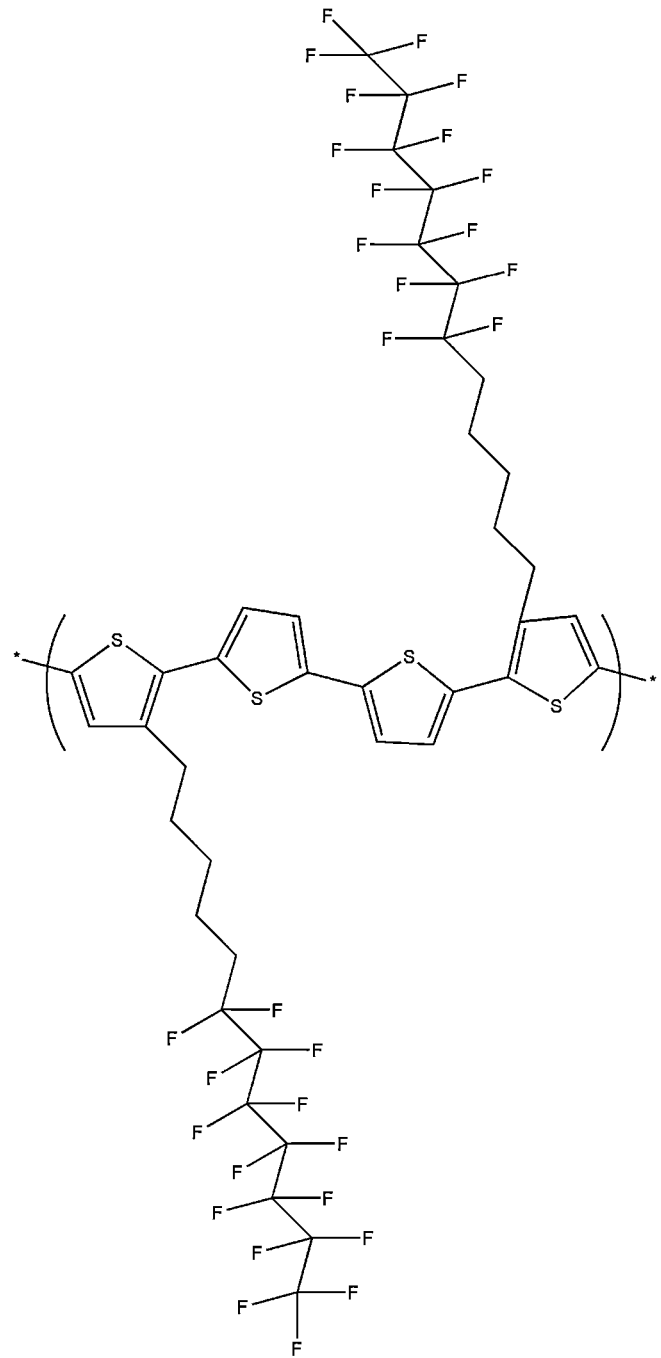
FIG. 1 shows a structure of a polymer according to one embodiment of the present invention, wherein a repeat number of repeat units is omitted for convenience.

Hereinafter, embodiments of the present invention will be described in detail with reference to the accompanying drawings.

In accordance with one aspect of the present invention, a π-conjugated compound represented by Formula 1 is provided:

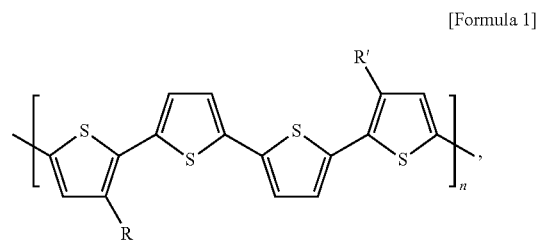

[Formula 1]

wherein R and R' are the same or different, each independently a $C_8$ to $C_{16}$ linear alkyl group, and composed of a fluorine-unsubstituted alkyl group and a fluorine-substituted alkyl group, wherein the fluorine-unsubstituted alkyl group is an alkyl group coupled to a thiophene ring of Formula 1; the fluorine-substituted alkyl group is an alkyl groups in which all hydrogens bonded to carbon are substituted with fluorine, and is coupled to the fluorine-unsubstituted alkyl group to constitute terminals of R and R' linear alkyl groups; a carbon number of the fluorine-substituted alkyl group is 0.5 to 2 times the carbon number of the fluorine-unsubstituted alkyl group; and n is an integer of 2 or more.

In the present invention, it is confirmed that a structure in which hydrogen of only a terminal of an alkyl group coupled to a thiophene ring is substituted with fluorine exhibits significantly increased hole mobility, and significantly improved properties in terms of thermal stability and chemical stability, as compared to a structure in which all hydrogens of the alkyl group are substituted with fluorine, or in which hydrogen of the terminal of the alkyl group is not substituted with fluorine and hydrogens of only a remaining portion excluding the terminal are substituted with fluorine.

According to one embodiment, in the π-conjugated compound represented by Formula 1, R and R' are the same, and the carbon number of the fluorine-substituted alkyl group is 1 to 2 times the carbon number of the fluorine-unsubstituted alkyl group.

That is, it is desirable that the carbon number of a fluorine-substituted terminal is 1 to 2 times the carbon number of a fluorine-unsubstituted thiophene coupling portion. In this regard, it is confirmed that an unexpected effect of improving hole mobility can be obtained in the case where thermal annealing is not performed, when the compound is dissolved in a solvent or dispersed in a dispersion medium.

In accordance with another aspect of the present invention, a π-conjugated compound represented by Formula 2 is provided:

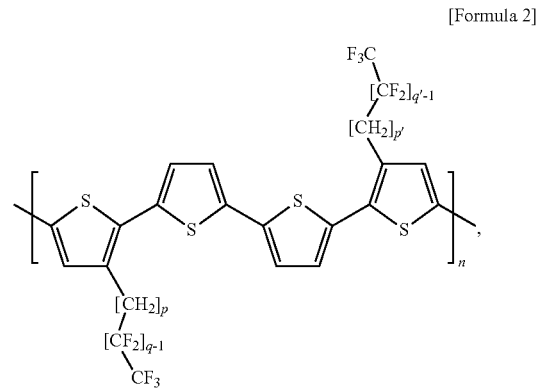

[Formula 2]

wherein p and p' are a repeat number of fluorine-unsubstituted alkylene, are the same or different, and are each independently an integer from 3 to 7; (q−1) and (q'−1) are a repeat number of difluoroalkylene, are the same or different, and are each independently an integer from 4 to 8; (p+q) is an integer from 8 to 16; (p'+q') is an integer from 8 to 16; q/p has a value between 1 and 2; q'/p' has a value between 1 and 2; and n is an integer from 2 to 5,000,000.

According to one embodiment, in the π-conjugated compound represented by Formula 2, p and p' are the same, and q and q' are the same.

According to another embodiment, it is desirable that, in the π-conjugated compound represented by Formula 2, p and p' be an integer from 4 to 6, and q and q' be an integer from 6 to 8. In this regard, it is confirmed that a bi-layer can be prepared since a polymer thin film dipped in a general solvent is not dissolved regardless of types of the general solvent after formation of the thin film so long as temperature of the solvent is not increased.

According to a further embodiment, it is more desirable that, in the π-conjugated compound represented by Formula 2, p, p', q and q' be each 5, 5, 7, 7. In this case, there are advantages that all of general solvents and fluorine-based solvents can be applied to the compound, and that a fluorophilic effect and a fluorophobic effect between the solvents and molecules of the polymer can be induced.

In accordance with yet another aspect of the present invention, a conductive organic thin film includes the π-conjugated compound according to embodiments of the present invention.

In accordance with yet another aspect of the present invention, an organic field effect transistor includes: a source electrode; a drain electrode; a gate electrode; a gate insulating layer; and an organic semiconductor layer, wherein the organic semiconductor layer includes the aforementioned conductive organic thin film.

In accordance with yet another aspect of the present invention, a method for preparing the π-conjugated compound represented by Formula 2 includes:

(a) obtaining a compound represented by Formula 5 by reacting a compound represented by Formula 3 with a compound represented by Formula 4:

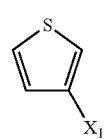

[Formula 3]

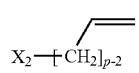

[Formula 4]

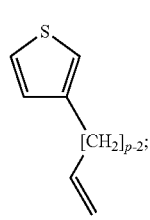

[Formula 5]

(b) obtaining a compound represented by Formula 7 by reacting the compound represented by Formula 5 with a compound represented by Formula 6:

[Formula 6]

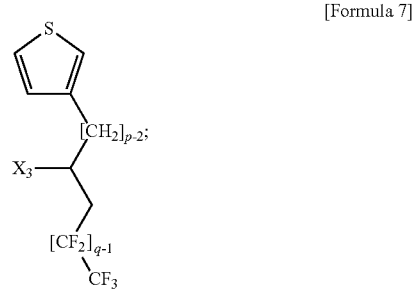

[Formula 7]

(c) obtaining a compound represented by Formula 8 by reducing the compound represented by Formula 7:

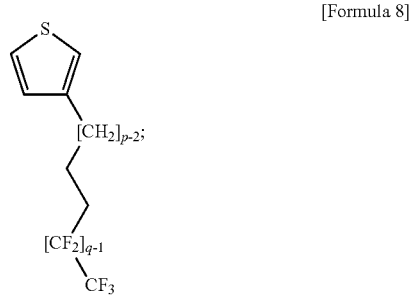

[Formula 8]

(d) obtaining a compound represented by Formula 9 by substituting one hydrogen in the compound represented by Formula 8 with $X_4$:

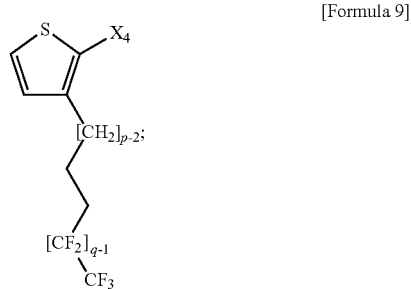

[Formula 9]

(e) obtaining a compound represented by Formula 10 by coupling the compounds represented by Formula 9 to each other:

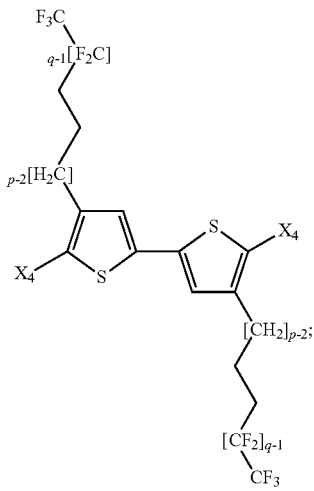

and (f) obtaining a compound represented by Formula 2 by coupling a compound represented by Formula 11 to the compound represented by Formula 10:

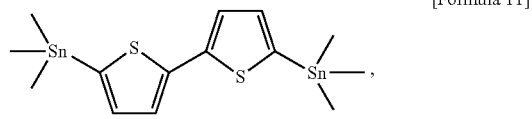

[Formula 11]

wherein p and p' are the same, and q and q' are the same; p is an integer from 3 to 7, and q is an integer from 5 to 9; q/p has a value between 1 and 2, and q'/p' has a value between 1 and 2; n is an integer from 2 to 5,000,000; and $X_1$, $X_2$, $X_3$ and $X_4$ are the same or different, and each independently selected from among Br, Cl and I.

In the method for preparing the π-conjugated compound according to one embodiment, operation (a) is performed in diethyl ether as a polar solvent using Kumada coupling in order to stabilize formation of Grignard complexes; operation (b) is performed under anhydrous conditions using radical reactions in order to prevent annihilation of radicals; operation (c) is performed using $NaBH_4$, which is a reducing agent, in order to remove iodine; operation (d) is performed under weak acid conditions using N-bromosuccinimide (NBS) in order to substitute bromine at the C-2 position of theophene; operation (e) is performed in polar solvent using a palladium (Pd) catalyst; and operation (f) is performed under a nitrogen atmosphere using Stille cross coupling.

In accordance with yet another aspect of the present invention, a method for preparing a conductive organic thin film includes: (A) preparing the π-conjugated compound represented by Formula 2 according to embodiments of the present invention; (B) obtaining a solution or liquid dispersion of the π-conjugated compound by introducing the π-conjugated compound into a solvent or dispersion medium and dissolving or dispersing the same; and (C) dipping a substrate into the solution or liquid dispersion and then drying the substrate after removing the same therefrom.

According to one embodiment, the solvent or dispersion medium is preferably selected from among dichlorobenzene (DCB), trichlorobenzene (TCB), hexafluorobenzene (HFB), and mixtures thereof. This is because the thin films can be prepared using only dip-coating instead of spin-coating without thermal annealing, thereby realizing large area devices.

According to another embodiment, operation (B) is preferably performed without thermal annealing, for example, at a temperature from 10° C. to 40° C. In this regard, it is confirmed that, when the above solvents or dispersion media are used, thermal annealing makes it difficult to realize large area devices using only dip-coating, which can be realized by the present invention.

With regard to a position of fluorinated carbon and a degree of fluorination, it is confirmed that, if fluorine is substituted to carbon adjoining or close to carbon of a substituted portion of thiophene instead of carbon of a terminal among carbon atoms included in the linear alkyl group coupled to thiophene, the overall energy level of the compound can be changed, and thus, the position of fluorinated carbon and the degree of fluorination described herein are important.

In addition, although it is important that fluorine is substituted to carbon of the terminal among carbon included in the linear alkyl group coupled to thiophene, other elements similar to fluorine in terms of electron affinity and atom size may be substituted thereto.

Now, the present invention will be described in detail with reference to some examples. However, it should be understood that these examples are provided for illustration only and are not to be in any way construed as limiting the present invention, and that various modifications, changes, and alterations can be made by those skilled in the art without departing from the spirit and scope of the invention.

EXAMPLES

Although existing PQT-12 polymers have dodecyl alkyl chains consisting of only hydrocarbons, an SFA-PQT polymer according to the present invention may improve interaction between polymer chains through a fluorophillic effect by substituting the hydrocarbons with semi-fluorinated linear alkyl chains. One compound of the SFA-PQT polymer is a polymer shown in FIG. 1, and a repeat number of repeat units is omitted for convenience. A process of preparing the polymer is shown in Reaction Formula 1:

[Reaction Formula 1]
Synthetic scheme
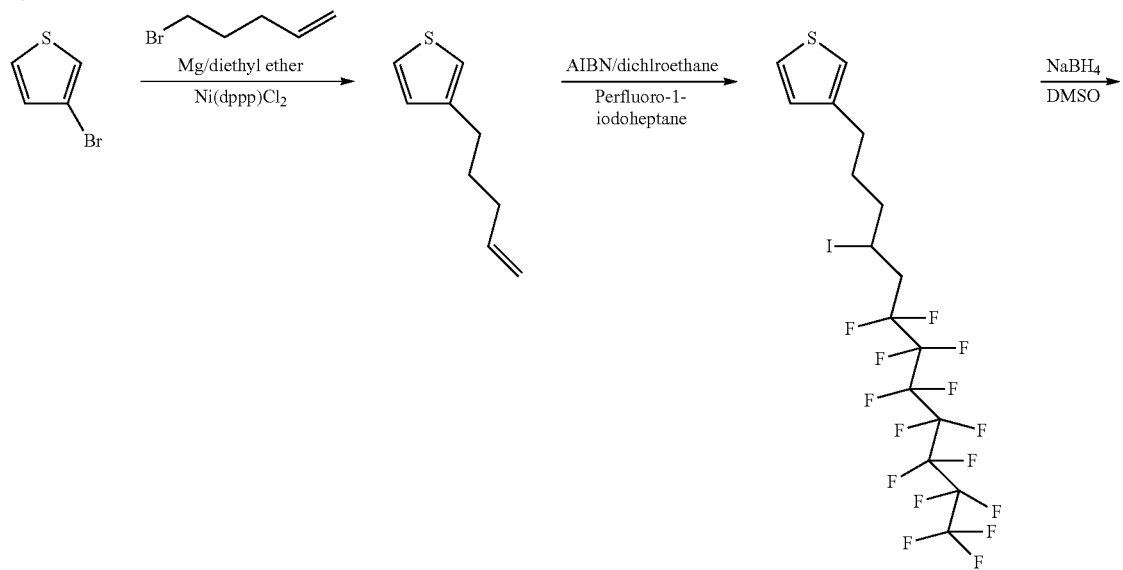
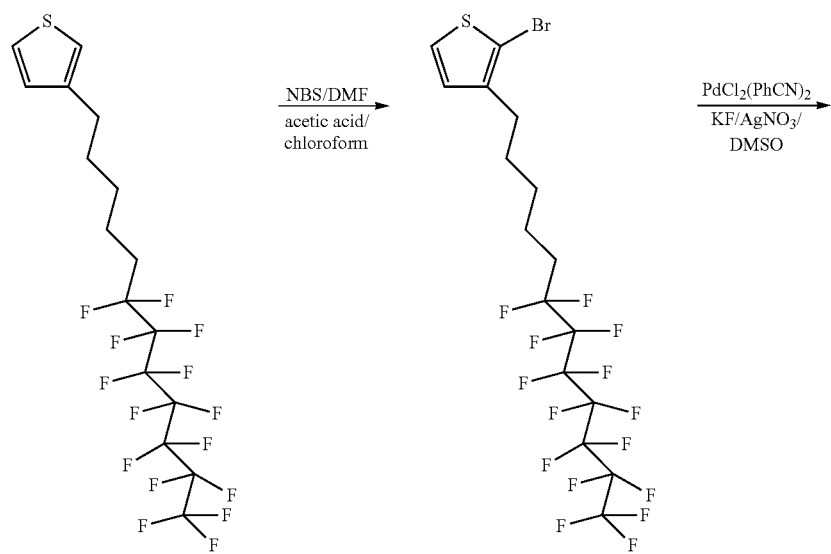

-continued
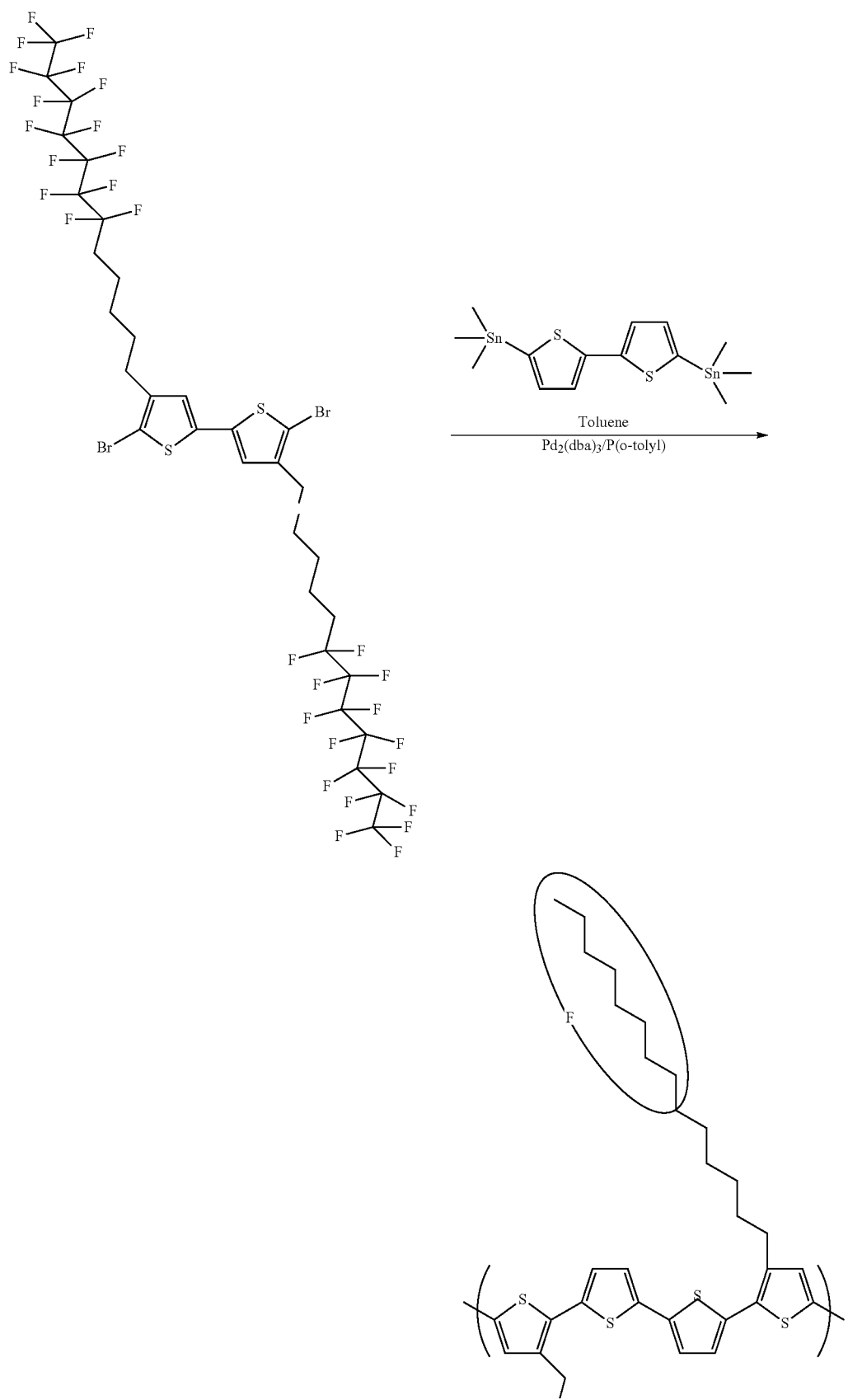

-continued

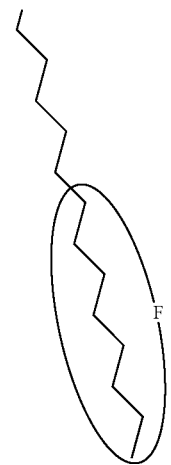

High-temp GPC (TCB)
Mn: 18,800
Mw: 26,100
PDI: 1.39

Figure 2:
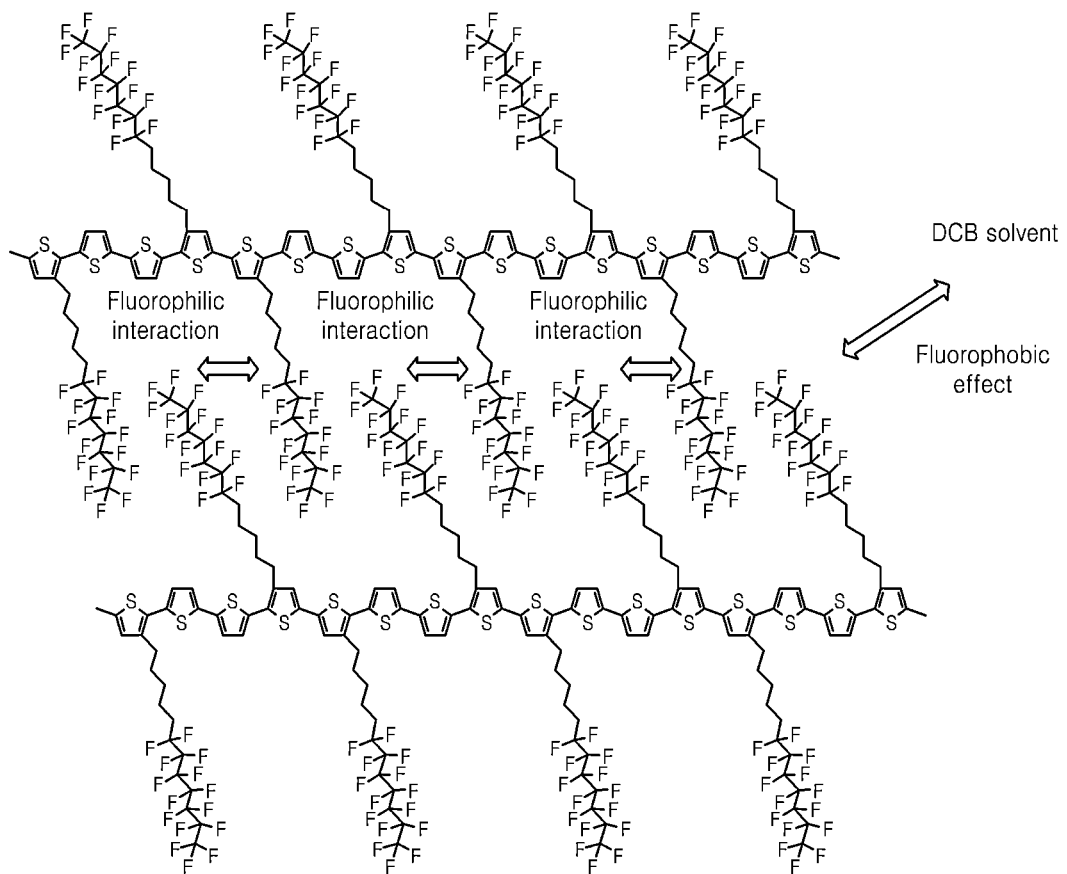
FIG. 2 is a mimetic diagram of segregation of SFA-PQT polymer in a DCB solvent.

In an inventive example, an SFA-PQT polymer solution was prepared using 1,2-dichlorobenzene (DCB), which does not interact with fluorine molecules, as a solvent, and a thin film was formed using the SFA-PQT polymer solution. In this case, it was confirmed that the polymer chains were packed with each other by fluorophillic interaction therebetween, and formed a fibril structure, in which holes can easily move, by the fluorophillic effect between polymer chains and the DCB solution (FIG. 2).

In a comparative example, the thin film was prepared using hexafluorobenzene (HFB), which can interact with fluorine molecules, as a solvent. In this case, since the SFA-PQT polymer strongly interacts with the HFB solvent, the polymer chains were uniformly distributed instead of forming a fibril structure. From results of observation of a surface of the SFA-PQT polymer thin film using AFM equipment, it was confirmed that the thin film employing the DCB solvent showed morphology of a noodle structure, and the thin film employing the HFB solvent showed flat morphology without particular features.

Further, in OFET devices using the DCB solvent, the fibril structure formed by the fluorophillic and fluorophobic effects exhibited a maximum hole mobility of 0.36 cm²/Vs without annealing, and this result shows that the SFA-PQT polymer according to the inventive example has about 2 times higher hole mobility than the existing PQT-12 polymers even though the process is simplified without additional thermal annealing.

Since a simple dip-coating process is used in preparation of OFET devices using the SFA-PQT polymer instead of spin-coating, by which a large amount of raw material is wasted, there is a merit that numerous devices can be rapidly prepared.

Although the polymer thin films are generally formed in a nitrogen atmosphere to prevent oxidation of the films, it was confirmed that an OFET device prepared by dipping the substrate into the heated SFA-PQT solution under atmospheric conditions exhibited excellent hole mobility. Particularly, it was confirmed that even though the OFET device prepared using dip-coating was left for 123 days under atmospheric conditions to test real oxidation stability, results showed little change in transistor characteristics.

Due to hydrophobic properties of the semi-fluorinated chains, it is supposed that the semi-fluorinated chains move up to the surface of the thin film, thereby improving oxidation stability of the OFET device. In addition, it is predicted that, with this property, there will be the same effect as in the above when the semi-fluorinated chains are applied to polymers of another structure.

Figure 3:
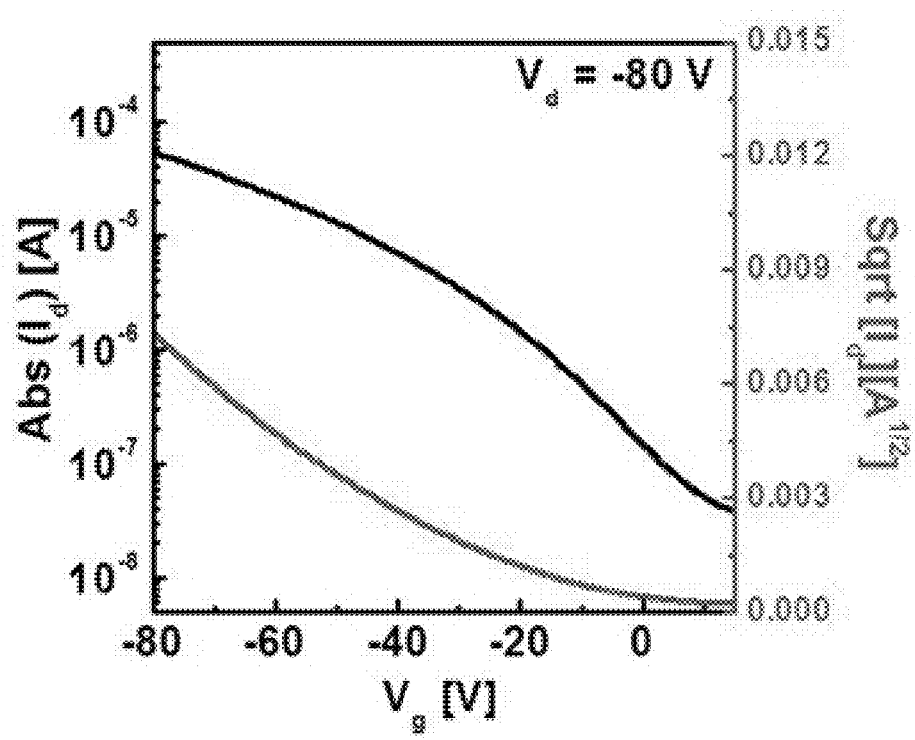
FIG. 3 shows transfer curves of an OFET device with SFA-PQT as the semiconductor.
Figure 4:
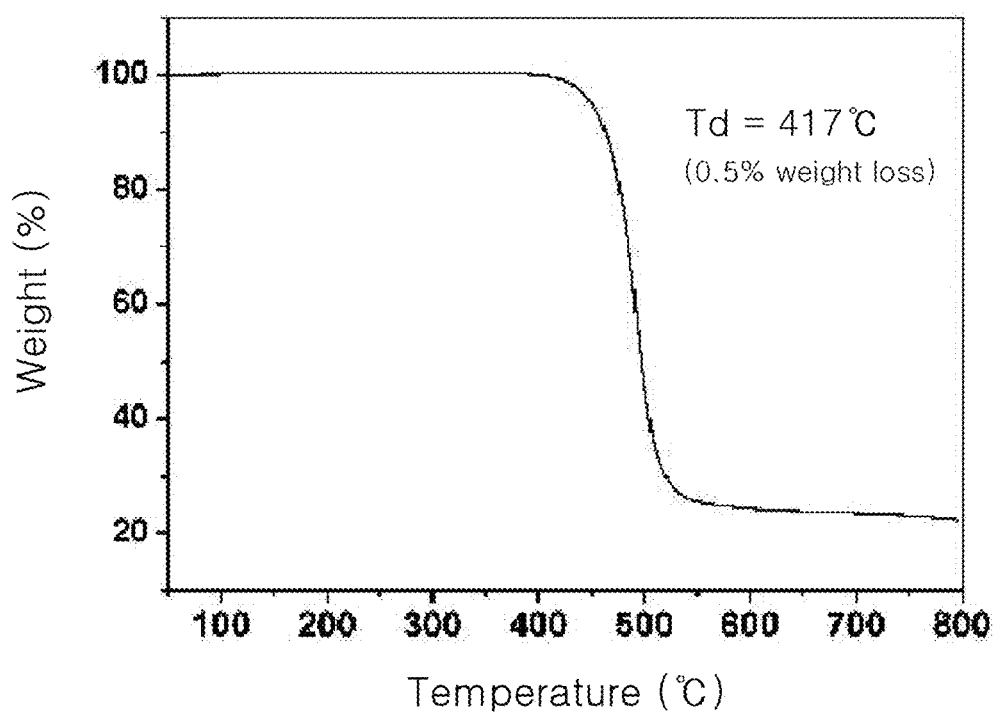
FIG. 4 shows weight loss Td of the SFA-PQT was 417° C., demonstrating significant improvement in thermal stability.
Figure 5A:
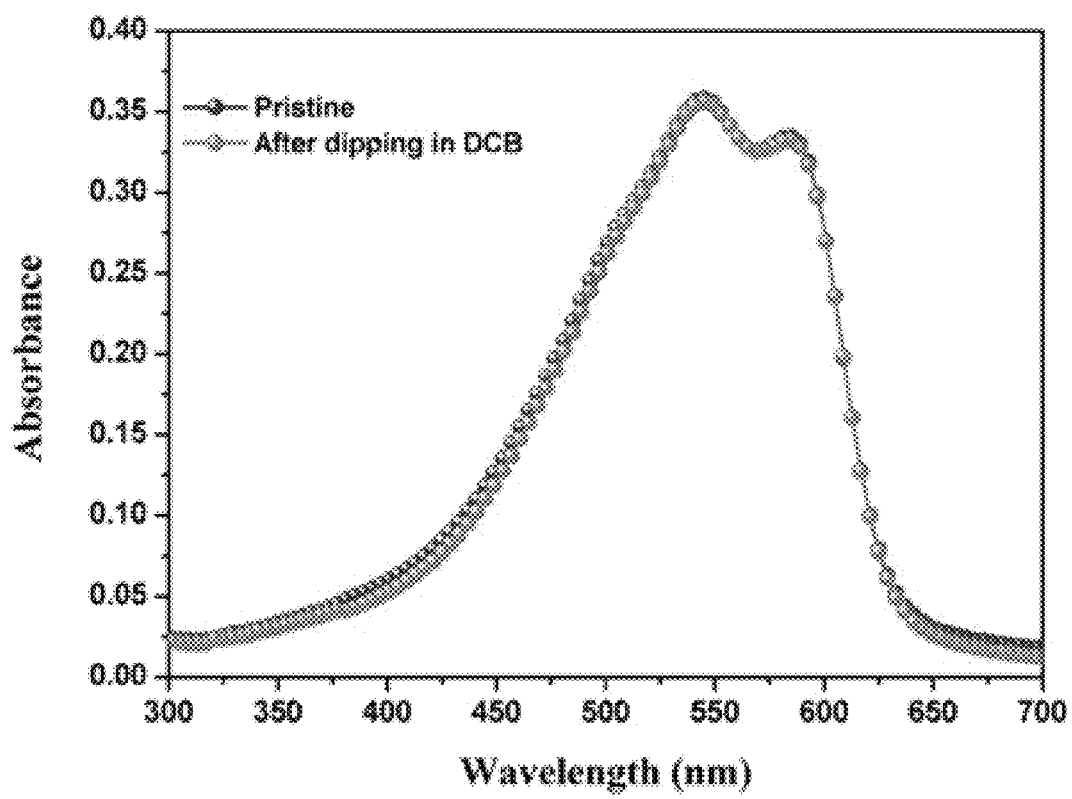
FIG. 5 shows UV-vis absorption intensity changes of SFA-PQT thin films before and after immersion into (a) dichlorobenzene and (b) 1,4-Bis(trifluoromethyl)benzene at room temperature for 1 hour.
Figure 5B:
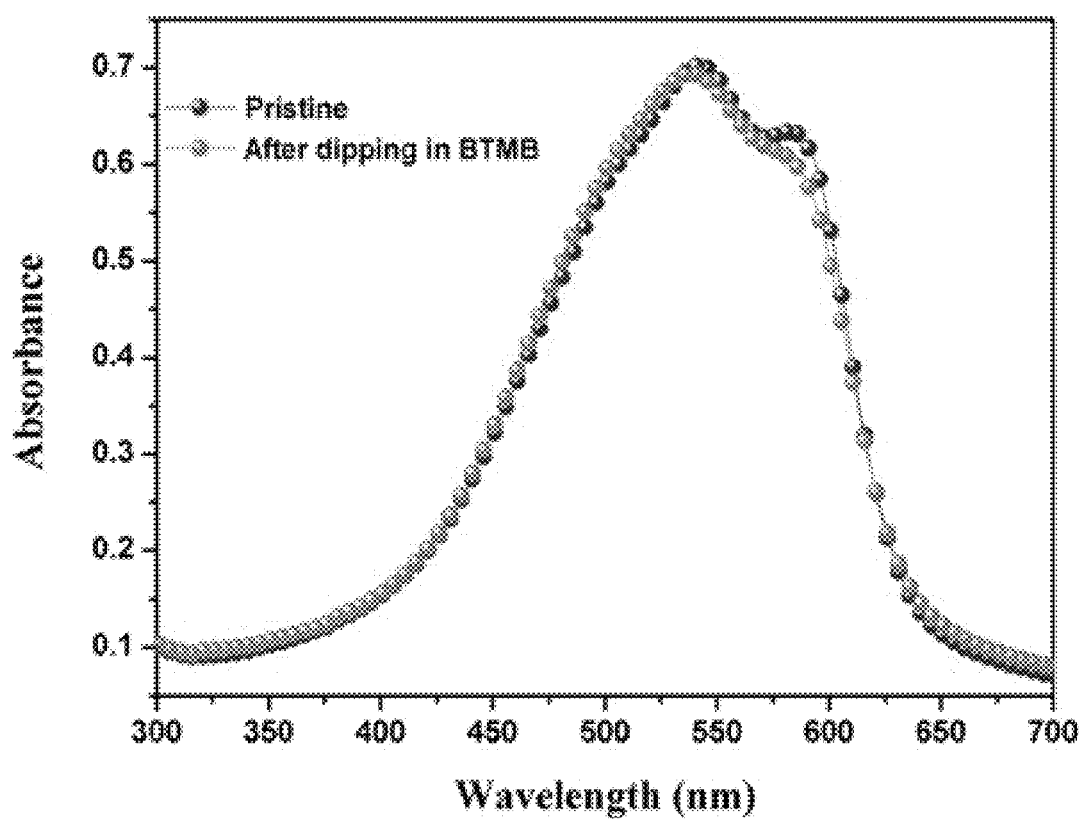
Figure 6A:
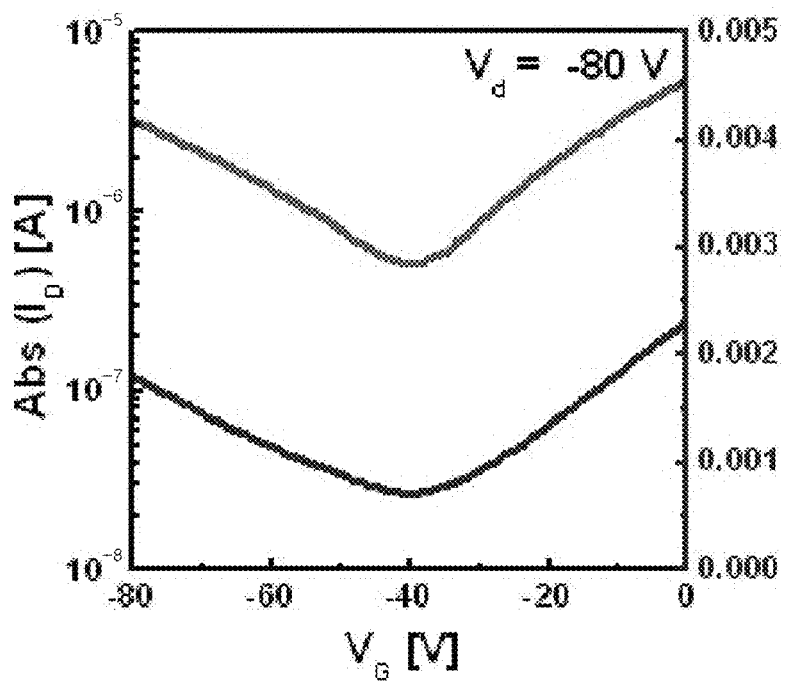
FIG. 6 shows transfer curves of an ambipolar transistor with a bilayer structure of (a) SFA-PQT and (b) P(NDI2OD-T2).
Figure 6B:
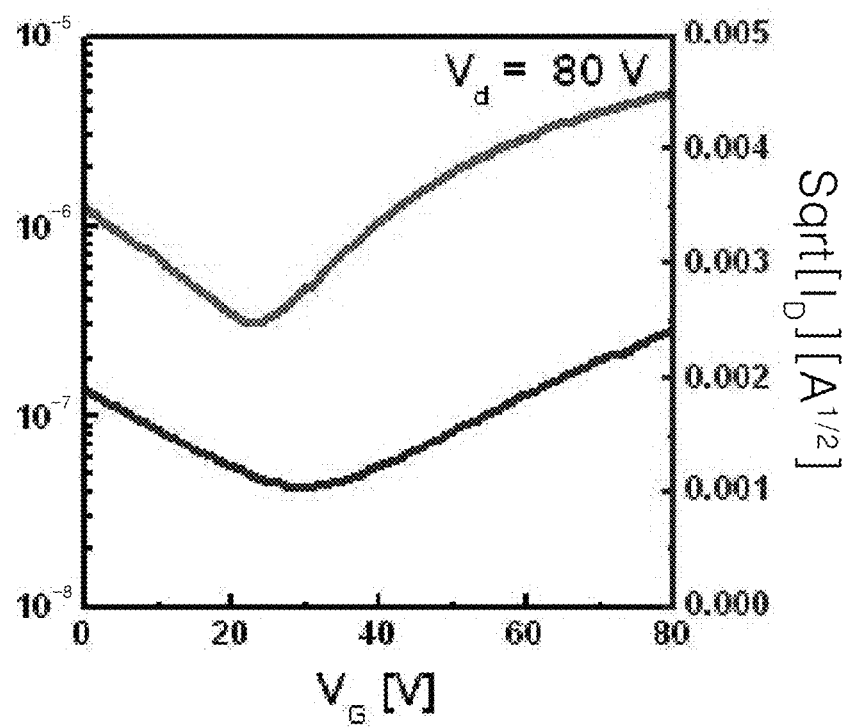
Figure 7:
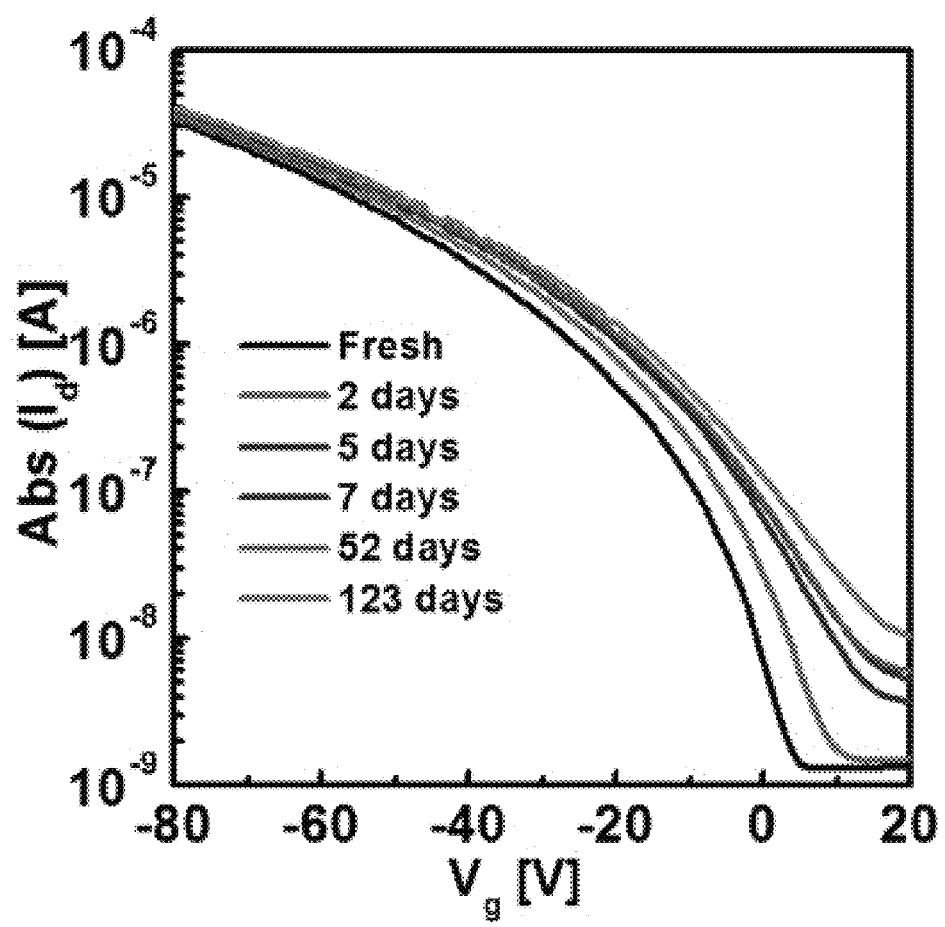
FIG. 7 shows a change in a transfer curve of a transistor using the SFA-PQT polymer depending on exposure time to air.

Result data of the polymer prepared in the inventive example is as follows:

1. It was confirmed that hole mobility was significantly increased to 0.36 cm²/Vs without annealing (FIG. 3);

2. It was confirmed that 0.5% weight loss $T_d$ of the SFA-PQT was 417° C., demonstrating significant improvement in thermal stability, whereas $T_d$ of the PQT-12 was in the range of 230° C. to 260° C. (FIG. 4);

3. It was confirmed that the polymer was not dissolved in a general solvent by confirming that UV-Vis absorption of the polymer was not decreased after being dipped into a general solvent for 1 hour (FIG. 5(a): DCB dichlorobenzene, FIG. 5(b): BTMB 1,4-bis(trifluoromethyl)benzene);

4. Ambipolar properties were confirmed after preparing a transistor by forming a N2200 (n-type) polymer bi-layer on the SFA-PQT (p-type) polymer thin film (FIG. 6: formation of a bi-layer is possible); and 5. FIG. 7 shows a change in a transfer curve of a transistor using the SFA-PQT polymer depending on exposure time to air.

Figure 8:
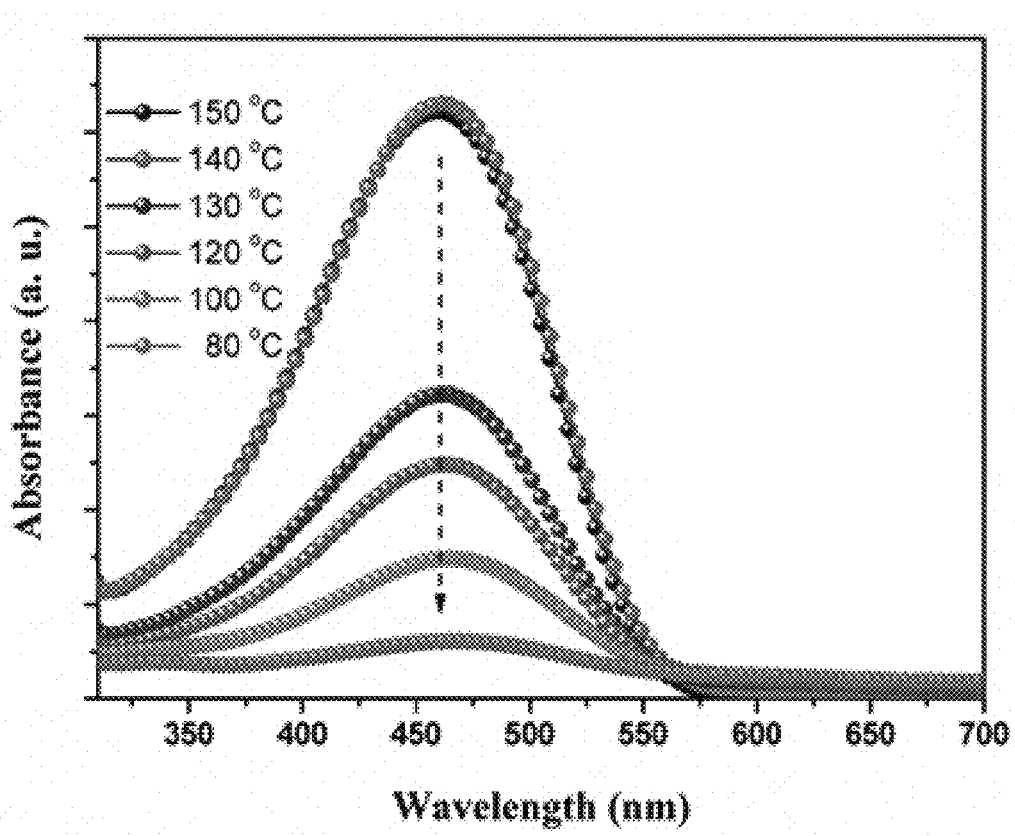
FIG. 8 shows UV-vis absorption spectra of SFA-PQT solution in DCB at different cuvette temperatures.

6. FIG. 8 shows a thermally reversible soluble-insoluble property of the SFA-PQT polymer. The SFA-PQT polymer was completely soluble in DCB solvent above 140° C., and SFA-PQT solution exhibited drastic solidification at temperature below 140° C. The property of the SFA-PQT polymer allowed the formation of a solution-processed bilayer structure and orthogonal processing with any solvent.

What is claimed is:

1. A π-conjugated compound represented by Formula 2:

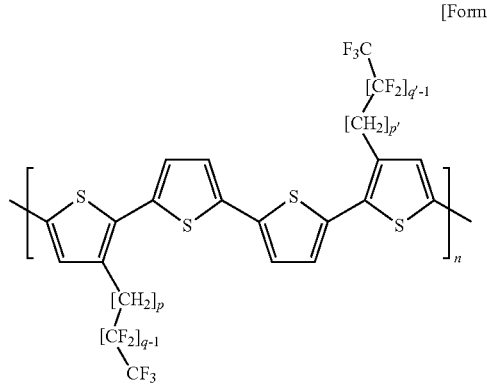

[Formula 2]

wherein p and p' are a repeat number of fluorine-unsubstituted alkylene, are the same or different, and are each independently an integer from 4 to 6;

(q−1) and (q'−1) are a repeat number of difluoroalkylene, are the same or different, and are each independently an integer from 4 to 8;

(p+q) is an integer from 8 to 16; (p'+q') is an integer from 8 to 16;

q/p has a value between 1 and 2; q'/p' has a value between 1 and 2; and n is an integer from 2 to 5,000,000.

2. The π-conjugated compound according to claim 1, wherein p and p' are the same, and q and q' are the same.

3. The π-conjugated compound according to claim 2, wherein q and q' are an integer from 6 to 8.

4. The π-conjugated compound according to claim 3, wherein p, p', q and q' are respectively 5, 5, 7, and 7.

* * * * *